(12) United States Patent
Gould et al.

(10) Patent No.: US 6,654,119 B1
(45) Date of Patent: Nov. 25, 2003

(54) SCANNING SPECTROPHOTOMETER FOR HIGH THROUGHPUT FLUROESCENCE DETECTION

(75) Inventors: Gene Gould, Cardiff, CA (US); Michael J. Conrad, Escondido, CA (US)

(73) Assignee: Chromagen, Inc., San Diego, CA (US)

( * ) Notice: Subject to any disclaimer, the term of this patent is extended or adjusted under 35 U.S.C. 154(b) by 0 days.

(21) Appl. No.: 09/552,803

(22) Filed: Apr. 20, 2000

Related U.S. Application Data

(60) Provisional application No. 60/130,438, filed on Apr. 21, 1999.

(51) Int. Cl.[7] ............................ G01N 21/64; G01J 3/18
(52) U.S. Cl. ...................... 356/318; 356/333; 250/458.1
(58) Field of Search ................................ 356/317, 318, 356/333, 334, 417; 250/458.1, 459.1, 461.1, 461.2

(56) References Cited

U.S. PATENT DOCUMENTS

| | | | |
|---|---|---|---|
| 2,940,355 A | * | 6/1960 | Cary ........................... 356/332 |
| 3,586,442 A | | 6/1971 | Tripp |
| 3,698,795 A | | 10/1972 | Flint |
| 3,715,585 A | | 2/1973 | Harrick |
| 3,730,626 A | | 5/1973 | Cruvellier et al. |
| 3,748,040 A | | 7/1973 | Hawes |
| 3,749,498 A | | 7/1973 | Shimomura |
| 3,807,862 A | | 4/1974 | Hatzenbuhler |
| 3,825,762 A | | 7/1974 | White |
| 3,832,555 A | | 8/1974 | Ohnishi |
| 3,865,490 A | | 2/1975 | Grossman |
| 3,886,363 A | | 5/1975 | Ohnishi et al. |
| 3,888,590 A | | 6/1975 | White |
| 3,915,571 A | | 10/1975 | Winter |
| 3,936,191 A | | 2/1976 | Chupp |
| 3,947,302 A | | 3/1976 | Grossman |
| 3,951,526 A | | 4/1976 | Grossman |
| 4,017,185 A | | 4/1977 | Chupp |
| 4,036,558 A | | 7/1977 | Pouey |
| 4,068,953 A | | 1/1978 | Harney et al. |
| 4,068,954 A | | 1/1978 | Da Silva |
| 4,095,897 A | | 6/1978 | Tsunazawa et al. |
| 4,102,576 A | | 7/1978 | Maeda et al. |
| 4,135,816 A | | 1/1979 | Niemann et al. |
| 4,311,387 A | | 1/1982 | deMey et al. |
| 4,540,282 A | * | 9/1985 | Landa et al. ................. 356/334 |
| 4,546,256 A | * | 10/1985 | Denisov et al. ............. 356/333 |
| 4,678,326 A | | 7/1987 | Harjunmaa |
| 4,973,159 A | | 11/1990 | Sohma et al. |
| 5,018,866 A | | 5/1991 | Osten |
| 5,847,400 A | | 12/1998 | Kain et al. |

FOREIGN PATENT DOCUMENTS

JP  63-289427  11/1988

OTHER PUBLICATIONS

Jobin Yvon, SPEX, "How to Build a Spectrfluorometer", undated.
Jobin Yvon, SPEX, "How to Select a Spectrfluorometer", Aug. 1994.
"SPECTAmax GEMINI Dual–scanning Microplate Spectrfluorometer", Aug. 17, 1998.

* cited by examiner

*Primary Examiner*—F. L. Evans
(74) *Attorney, Agent, or Firm*—Pillsbury Winthrop LLP

(57) ABSTRACT

A fluorescence spectrophotometer having an excitation double monochromator, a coaxial excitation/emission light transfer module, and an emission double monochromator. Each monochromator includes a pair of holographic concave gratings mounted to precisely select a desired band of wavelengths from incoming broadband light without using other optical elements, such as mirrors. Selected excitation light is directed into a sample well by a light transfer module that includes a coaxial excitation mirror positioned to direct excitation light directly to the bottom of a well of a multi-well plate. Fluorescence emission light that exits the well opening is collected by a relatively large coaxial emission mirror. The collected emission light is wavelength selected by the emission double monochromator. Selected emission light is detected by a photodetector module.

14 Claims, 7 Drawing Sheets

SCANNING SPECTROPHOTOMETER FOR HIGH THROUGHPUT FLUROESCENCE DETECTION

CROSS-REFERENCE TO RELATED APPLICATION

This application claims benefit of the priority of U.S. Provisional Application Serial No. 60/130,438, filed Apr. 21, 1999 and entitled "Novel Scanning Spectrophotometer For High Throughput Fluorescence Detection."

TECHNICAL FIELD

This invention relates to wavelength scanning fluorescence spectrophotometers using dual grating monochromators, but not optical filters, to select excitation and emission wavelengths of light and to detect and quantify simultaneous fluorescence emission from multiple fluorophores in the same sample.

BACKGROUND

Definitions:

1) Fluorescence: The result of a multi-stage process of energy absorption and release by electrons of certain naturally occurring minerals, polyaromatic hydrocarbons and other heterocycles.

2) Excitation: photons of energy, $e=h\nu_{exc}$, are supplied by a light source and absorbed by an outer electron of a fluorophore, which is elevated from the ground state, $S_0$, to an excited electronic singlet state, $S'_1$.

3) Excited State Lifetime: An excited electron remains in the singlet state for a finite period, typically from 1 to 20 nanoseconds, during which the fluorophore undergoes a variety of changes including conformational changes and alterations in the interaction with solvent. As a result of these changes, the energy of the $S'_1$ singlet electron partially dissipates to a relaxed singlet excited state, $S_1$, from which fluorescence emission of energy occurs, returning the electron to the ground state, $S_0$.

4) Emission: photons of energy, $e=h\nu_{em}$, are released from an excited state electron, which returns the fluorophore to the ground state. Owing to energy loss during the excited state lifetime, the energy of these photons is lower than that of the exciting photons, and the emitted light is of longer wavelength. The difference in the energy (or wavelengths) is called the Stoke's shift and is an important feature in the selection of a dye for use as a label or in a probe. The greater the Stoke's shift, the more readily low numbers of photons can be distinguished from background excitation light.

5) Fluorophores: Fluorescent molecules are generally referred to as fluorophores. When a fluorophore is utilized to add color to some other molecule, the fluorophore is called a fluorescent dye and the combination is referred to as a fluorescent probe. Fluorescent probes are designed to: 1) localize and help visualize targets within a specific region of a biological specimen, or, 2) respond to a specific stimulus.

6) Electromagnetic Spectrum: the entire spectrum, considered as a continuum, of all kinds of electric and magnetic radiation, from gamma rays, having a wavelength of 0.001 Angstroms to long waves having a wavelength of more than 1,000,000 kilometers and including the ultraviolet, visible and infrared spectra.

7) Fluorescence Spectrum: Unless a fluorophore is unstable (photobleaches), excitation and emission is a repetitive process during the time that the sample is illuminated. For polyatomic molecules in solution, discrete electronic transitions are replaced by broad energy bands called the fluorescence excitation and fluorescence emission spectra, respectively.

8) Monochromator: A device which admits a wide spectral range of wavelengths from the electromagnetic spectrum via an entrance aperture, and, by dispersing wavelengths in space, makes available at an exit aperture only a narrow spectral band of prescribed wavelength(s). Optical filters differ from monochromators in that they provide wavelength selection through transmittance of selected wavelengths rather than through spatial dispersion. A second distinguishing feature of a monochromator is that the output wavelength(s), and in many cases, the output spectral bandwidth, may be continuously selectable. Typically, the minimal optical components of a monochromator comprise:

(a) an entrance slit that provides a narrow optical image;
(b) a collimator which ensures that the rays admitted by the slit are parallel;
(c) some component for dispersing the admitted light into spatially separate wavelengths;
(d) a focusing element to re-establish an image of the slit from selected wavelengths; and,
(e) an exit slit to isolate the desired wavelengths of light.

In a monochromator, wavelength selection is achieved through a drive system that systematically pivots the dispersing element about an axis through its center. Slits are narrow apertures in a monochromator which may have adjustable dimensions. Slits effect selection of the desired wavelength(s) and their dimensions may be adjustable.

9) Double Monochromator: Two monochromators coupled in series. The second monochromator accepts wavelengths of light selected by the first and further separates the prescribed wavelengths from undesired wavelengths.

10) Wavelength Scanning: Continuous change of the prescribed output wavelength(s) leaving the exit slit of a monochromator. In a spectrophotometer, wavelengths of the electromagnetic spectrum are scanned by the excitation monochromator to identify or prescribe the wavelength(s) at which a fluorophore is excited; wavelength scanning by the emission monochromator is used to identify and detect the wavelength(s) at which a fluorophore emits fluorescent light. In automated fluorescence spectrophotometers, wavelength scanning by the excitation and emission monochromators may be performed either separately or concurrently (synchronous scanning).

11) Area Scanning: Area scanning is distinct from wavelength scanning and is the collective measurement of local fluorescence intensities in a defined two dimensional space. The result is an image, database or table of intensities that maps fluorescence intensities at actual locations in a two dimensional sample. At its simplest, area scanning may be a photograph made with a camera in which all data are collected concurrently. Alternatively, the sample may be moved past a detector which measures the fluorescence in defined sub-areas of a sample. The collected information creates a matrix which relates fluorescence intensity with position from which an image, table or graphical representation of the fluorescence in the original sample can be created.

12) Fluorescence Detectors

Five elements of fluorescence detection have been established through laboratory use of fluorophores during the last two decades:

(a) an excitation source,
(b) a fluorophore,
(c) some type of wavelength discrimination to isolate emission photons from excitation photons, (d) some type of photosensitive response element that converts emission photons into a recordable form, typically an electronic signal or a photographic image, and, (e) a light tight enclosure to restrict ambient light.

Fluorescence detectors are primarily of four types, each providing distinctly different information:

(a) Cameras resolve fluorescence as spatial coordinates in two dimensions by capturing an image: [a] as a photographic image on highly sensitive film, or, [b] as a reconstructed image captured on arrays of pixels in a charge coupled device (CCD).

(b) Fluorescence microscopes also resolve fluorescence as spatial coordinates in two or three dimensions. Microscopes collect all of the information for an image for a prescribed visual field at the same time without any movement of either the sample or the viewing objective. A microscope may introduce qualitative estimation of fluorophore concentration through use of a camera to capture an image in which case the measure is a function of exposure time.

(c) Flow cytometers measure fluorescence per biological cell in a flowing liquid, allowing subpopulations within a mixture of cells to be identified, quantitated and in some cases separated. Flow cytometers cannot be used to create an image of a defined area or perform wavelength scanning. The excitation light source is invariably a laser and wavelength discrimination is accomplished through some combination of tunable dye lasers and filters. Although these instruments may employ photomultiplier tubes to detect a measurable signal, there are no flow cytometers that employ monochromators for wavelength scanning.

(d) Spectrofluorometers (spectrophotometer(s)) typically employ a PMT to detect fluorescence but can measure either: [a] the average current evoked by fluorescence over time (signal averaging), or, [b] the number of photons per unit time emitted by a sample (photon counting).

Fluorescence spectrophotometers are analytical instruments in which a fluorescent dye or probe can be excited by light at specific wavelengths, and, concurrently, have its emitted light detected and analyzed to identify, measure and quantitate the concentration of the probe. For example, a piece of DNA may be chemically attached, or labeled, with fluorescent dye molecules that, when exposed to light of prescribed wavelengths, absorb energy through electron transitions from a ground state to an excited state. As indicated above, the excited molecules release excess energy via various pathways, including fluorescence emission. The emitted light may be gathered and analyzed. Alternatively, a molecule of interest may be conjugated to an enzyme which can convert a specific substrate molecule from a non-fluorescent to a fluorescent product following which the product can be excited and detected as described above.

The ranges of excitation and emission wavelengths employed in a fluorescence spectrophotometer typically are limited to the ultraviolet and visible portions of the electromagnetic spectrum. For the purposes of fluorescence detection, useful dyes are those which are excited by, and emit fluorescence at, a few, narrow bands of wavelengths within the near ultraviolet and visible portions of the electromagnetic spectrum. Desired wavelengths for excitation of a specific fluorescent molecule may be generated from:

1) a wide band light source by passing the light through a series of bandpass filters (materials which transmit desired wavelengths of light and are opaque to others), or cut-on filters (materials which transmit all wavelengths longer or shorter than a prescribed value, 2) a narrow band light source such as a laser, or, 3) an appropriate monochromator.

For a wide band light source, the light to which a fluorescent dye is exposed is typically isolated through bandpass filters to select a desired wavelength from the ultraviolet or visible spectrum for use in excitation. In monochromator-based instruments, the wavelength of choice is obtained after light from the source has been dispersed into a spectrum from which the desired wavelength is selected. Whatever the light source, the fluorescence emission is typically isolated through bandpass filters, cut-on filters, or emission monochromators to select a desired wavelength for detection by removal of all light of any wavelengths except the prescribed wavelengths. Most fluorescence detection involves examination of specimens that are in a liquid phase. The liquid can be contained in a glass, plastic or quartz container which can take the form of, for example: an individual cuvette; a flow-through cell or tube; a microscope slide; a cylindrical or rectangular well in a multiwell plate; or silicon microarrays which may have many nucleic acids or proteins attached to their surfaces. Alternatively, the liquid can be trapped in a two-dimensional polyacrylamide or agarose gel. In each of these cases, light which has already passed through the optical filters to select the correct wavelengths for excitation illuminates the sample in the container or gel; concurrently, emitted light is also collected, passed through a second set of optical filters to isolate the wavelengths of emission, and then detected using a camera, or photosensor.

The optical filters used in fluorescence detectors present characteristics that limit the sensitivity, dynamic range and flexibility of fluorescence detection, including: light absorption which causes a loss of efficiency through the system; inherent auto-fluorescence, which produces a high background signal; transmission of other wavelengths outside the wavelengths of desired bandpass which, in turn limits both sensitivity and dynamic range. Optical filters must be designed and manufactured to select for discrete ranges of wavelengths ("center-width bandpasses") which limits fluorescence detection to the use of compounds which are excited and emit at wavelengths appropriate for those filters. Development of a new fluorescent dye with unusual spectral properties may necessitate design of a new excitation/emission filter pair.

To increase efficiency in fluorescence cuvette spectrophotometers as well as to provide continuous selection of wavelengths, it has been known to use grating or prism-based monochromators to disperse incoming light from an excitation source, select a narrow band of excitation wavelengths and, separately, to select an emission wavelength. Gratings come in many forms but are etched with lines that disperse broadband light into its many wavelengths. A monochromator typically includes a light-tight housing with an entrance slit and an exit slit. Light from a source is focused onto the entrance slit. A collimating mirror within the housing directs the received beam onto a flat optical grating, which disperses the wavelengths of the light onto a second collimating mirror which in turn focuses the now linearly dispersed light onto the exit slit. Light of the desired wavelength is selected by pivoting the grating to move the linear array of wavelengths past the exit slit, allowing only a relatively narrow band of wavelengths to emerge from the monochromator. The actual range of wavelengths in the selected light is determined by the dimensions of the slit.

The process of continuous selection of a narrow band of wavelengths from all wavelengths of a continuous spectrum is referred to as wavelength scanning and the angle of rotation of the dispersing optical grating with respect to the entrance and exit slits correlates with the output wavelength of the monochromator. In order to more precisely select the wavelengths of excitation and fluorescence detection, it has been known to use two gratings in each monochromator to enhance wavelength selection for both the excitation and emission light in a fluorescence spectrophotometer. While the monochromators potentially eliminate the need to use optical filters for wavelength selection and free the scientist from the limitations of filters, their use imposes other limitations on instrument sensitivity and design. For example, monochromators having the configurations described above have the disadvantage of requiring at least four mirrors and two dispersing elements, along with associated light blocking entrance and exit slits. Consequently, such devices have been relatively complex and comparatively inefficient compared to filter based instruments.

Analysis of multiple samples in multi-well plates is a highly specialized use of fluorescence spectrophotometers. Typically, the excitation light is introduced into a well from a slight angle above the well in order to allow the majority of the fluorescence emission light from the sample within a well to be collected by a lens or mirror. However, as the number of wells per plate is increased (e.g., from 96 wells per plate to in excess of 9600 per plate), this side illumination configuration becomes disadvantageous, since most of the incoming excitation light strikes the side of the well rather than the sample. Since such wells typically have black side walls, much of the excitation light is lost.

As mentioned above, one method employed to overcome the limitations of side illumination configurations has been use of an optical fiber to guide the excitation light to an illumination end of the fiber directly positioned over a well. A second bundle of fibers is employed to collect light from the well and transmit it to the PMT. In a variation of this design, a bifurcated optical fiber positioned above a microwell has been used to carry light both into and out of the well. However, optical fibers typically introduce absorption losses and may also auto-fluoresce at certain wavelengths. Accordingly, such a solution is not particularly efficient.

Another approach has been to use multi-well plates with transparent bottoms, and exposing a sample within a well to excitation light from the bottom while collecting emission light from the open top. While this approach has value in some circumstances, light is lost from absorption as well as from light scattering by the plastic at the well bottom.

Additionally, the transparent plate material may itself auto-fluoresce. In addition, well-to-well optical reproducibility of the well bottom material has not been achieved, which has limited the ability to correlate measurements on a well-to-well or plate-to-plate basis. Accordingly, such a solution has proven to be less efficient than illuminating and collecting light from the same side of a sample.

Examples of such prior art using fiber optic light paths include a single unit fluorescence microtiter plate detector (the "Spectromax GEMINI") introduced in 1998 by Molecular Devices, which employs a hybrid combination of single grating monochromators, filters, mirrors and optical fibers, and the "Fluorolog-3" a modular instrument and the "Skin-Sensor", a unitized instrument, produced by Instruments SA, both of which employ bifurcated fiber optic bundles to conduct light from an excitation monochromator and to collect light from a sample after which it is transmitted to the excitation monochromator.

It should be noted that microtiter plate applications of fluorescence monochromators are also limited to microwell plates with 384, 96 or fewer wells; that is, 1536-well microplates as well as "nanoplates" containing 2500 wells, 3500 wells and even 9600 wells cannot be used with the current fiber-optic/monochromator based instruments. Detectors for such plates typically use lasers and filters combined with confocal microscopy.

For the large number of applications involving glass microscope slides, polyacrylamide gels or standard 96-well, 384-well and 1536-well microwell plates, it would be desirable to have a fluorescence spectrophotometer that provides high efficiency, enables high precision continuous excitation and emission wavelength selection, provides significantly greater dynamic range, eliminates the use of optical filters and optical fibers (i.e., light paths do not pass through any optical materials other than air), and has a highly efficient structure for both guiding the excitation light onto a sample and collecting the emission light from the sample in a microtiter well or on a two dimensional surface such as a glass microscope slide, polyacrylamide gel, silicon microarray, or other solid surfaces.

In general, the measurement of fluorescent light intensity, the luminescence, is defined as the number of photons emitted per unit time. Fluorescence emission from atoms or molecules can be used to quantitate the amount of an emitting substance in a sample. The relationship between fluorescence intensity and analyte concentration is:

$$F = kQ_e P_o (1 - 10^{[\epsilon bc]})$$

where F is the measured fluorescence intensity, k is a geometric instrumental factor, Qe is the quantum efficiency (photons emitted/photons absorbed), $P_o$ is the probability of excitation which is a function of the radiant power of the excitation source, $\epsilon$ is the wavelength dependent molar absorptivity coefficient, b is the path length and c is the analyte concentration. In previous applications, the above equation was simplified by expanding the equation in a series and dropping the higher terms to give:

$$F = kQ_e P_o (2.303 \epsilon * b * c).$$

In the past, this relationship was acceptable because fluorescence intensity appeared to be linearly proportional to analyte concentration. The equation fails, however, to provide for true comparison of the fluorescence intensities of different fluorophores because measurement of fluorescence intensity is highly dependent upon k, the geometric instrumental factor.

Different types of detectors vary in both the time period during which a measurement is made and the speed at which each can discriminate between photons, characteristics which can be of critical importance when comparing the luminosity of two fluorophores. Consider two fluorescent dyes that differ only in that the excited state lifetime of one is tenfold longer than that of the excited state lifetime of the second fluorophore (e.g., 1 nanosecond and 10 nanoseconds, respectively). When detected using photographic film exposed for a defined exposure time, the dye with the shorter lifetime would clearly appear brighter on the exposed film. However, if a detector employing continuous excitation were used which could not discriminate between photons at a high enough frequency, the fluorophore with the shorter excited state lifetime could actually be emitting far more photons but the detector could erroneously indicate that the fluorescence intensity of the two dyes was the same.

Fluorescence is detected in spectrophotometers through generation of photocurrent in an appropriate photosensitive device such as a photomultiplier tube or other photosensing device, both of which are characterized by low levels of background or random electronic noise. For this reason, fluorescent emission processes are best characterized by Poisson statistics and fluorescence can be measured through either photon counting or signal averaging:

Photon counting is a highly sensitive technique for measurement of low levels of electromagnetic radiation. In photon counting detection, current produced by a photon hitting the anode of a photomultiplier tube with sufficient energy to begin an avalanche of electrons is tested by a discriminator circuit to distinguish between random electronic noise and true signal. At such light levels, the discreteness of photons dominates measurement and requires technologies that enable distinguishing electrical pulses that are photon-induced from dark-current impulses that originate in the detector (e.g., a photomultiplier tube) from other causes.

In previous applications of photon counting, the dynamic range of detection was restricted by the ability of the detector to discriminate between photons closely spaced in time. Additionally, the signal to noise ratio in photon counting is also a function of the light intensity. Assume a steady light flux incident on a photocathode producing m photoelectrons per second. During any one second, the light incident on the photocathode is, on average, m photoelectrons with a standard deviation of $m^{1/2}$. The signal to noise ratio in such measurements is:

$$S/N = m/m^{1/2} = m^{1/2} \tag{1}$$

Depending upon their frequency and energy, individual photoelectrons can be counted with a detector of sufficient gain but the precision of any measurement can never be better than the limit imposed by equation (1). In its simplest form, a practical photon counting instrument consists of a fast amplifier and a discriminator set to a low threshold relative to the input, typically −2 mV, which has been found empirically to correspond to the optimum compromise between susceptibility to electrical pickup and operating the photomultiplier at excessive gain.

Theoretically less sensitive than photon counting and with greater sensitivity to electronic drift, signal averaging uses photocurrent as a direct measure of the incident light signal. The noise associated with the photocurrent $I_k$, taking the system bandwidth (frequency of response), B, into account, is given by the shot noise formula:

$$S/N = (I_k/2eI_kB)^{1/2} \tag{2}$$

where e is the electronic charge. The forms of equations 1 and 2 are similar since they refer to the same phenomenon and predict essentially the same result. In contrast to photon counting, in which the signal is inherently digitized and its dynamic range limited by the speed of the timer counter, in equation 2 the signal is taken as a continuous variable of the photocurrent and it is possible to obtain a much larger dynamic range. In practice, however, the analog-to-digital conversion process severely limits the dynamic range owing to the slow response times associated with A/D converters having more than 16-bit resolution.

In general purpose fluorescence detection instruments, the light source can be a quartz halogen lamp, a xenon lamp or similar gas discharge lamp, a photodiode or one of many types of lasers. Typically the sample is exposed to continuous illumination which maintains a relatively stable percentage of the total number of fluorophores in an excited state. In these instruments, the cross-sectional dimension of the sample which is illuminated is principally determined by slits. In more complex instruments, including any using imaged light, confocal optics or point source illumination, the exciting light beam is shaped and focused by lenses and mirrors onto a single point and a single focal plane in the sample.

SUMMARY

According to various embodiments of the present invention, a wavelength and area scanning fluorescence spectrophotometer is provided that includes an excitation double monochromator, a coaxial excitation/emission light transfer module, an emission double monochromator a high speed timer-counter circuit board and a precision x-y-z mounting table for use in positioning a sample relative to the focal plane of the exciting light. Operations of each are directed and coordinated through a timer-counter board.

Each monochromator includes a pair of holographic concave gratings mounted to precisely select a desired band of wavelengths from incoming broadband light. Selected excitation light is directed into a sample well or onto a two dimensional surface such as a polyacrylamide gel or microscope slide by a light transfer module that includes a coaxial excitation mirror positioned to direct excitation light directly into a well of a multi-well plate or onto a particular area of a gel, microscope slide or microarray. Emitted light that exits the sample is collected by a relatively large front-surfaced mirror. The collected emission light is wavelength selected by the emission double monochromator. Both monochromators contain three precision matched slits that are positioned to restrict unwanted wavelengths while simultaneously creating a "near point" source of the desired wavelengths for the succeeding stage of the optical path. Emission light that has been isolated in this way is projected onto the photodetector module which converts the received energy into a digital representation of the fluorescence intensity of the sample.

One embodiment includes a fluorescence spectrophotometer system having a light source; a first double monochromator operating to separate and output selected wavelengths of light from the light source as excitation light; a light transfer module for directing substantially all of the excitation light directly onto a sample, and for collecting, focusing, and directing fluorescence from the sample as emission light; a second double monochromator operating to separate and output selected wavelengths of the emission light; and a photodetector and analyzer for detecting the selected wavelengths of emission light and outputting an indication of such detection.

Another embodiment includes a double monochromator having an entrance slit for accepting light; a first optical grating positioned to intercept and disperse the accepted light from the entrance slit; a first selection slit positioned to intercept at least part of the dispersed light from the first optical grating and select and pass a narrowed range of wavelengths from such dispersed light; a second optical grating positioned to intercept and disperse the passed light from the first selection slit; and a second selection slit positioned to intercept at least part of the dispersed light from the second optical grating and select and pass a narrowed range of wavelengths from such dispersed light.

Yet another embodiment includes a light transfer module having an input mirror, positioned coaxially with an area to be illuminated, for directing incoming light to illuminate the area; and an output mirror, positioned coaxially with the area to be illuminated and in reflective alignment with the input mirror, for collecting, focusing, and directing light emitted by the area upon illumination.

Another embodiment includes a photon counting photodetector and high speed timer-counter board which largely eliminates instrument drift, provides great sensitivity while enabling high frequency discrimination of photons for maximum resolution and quantitation and, concurrently, providing significantly greater dynamic range.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

Figure 1:
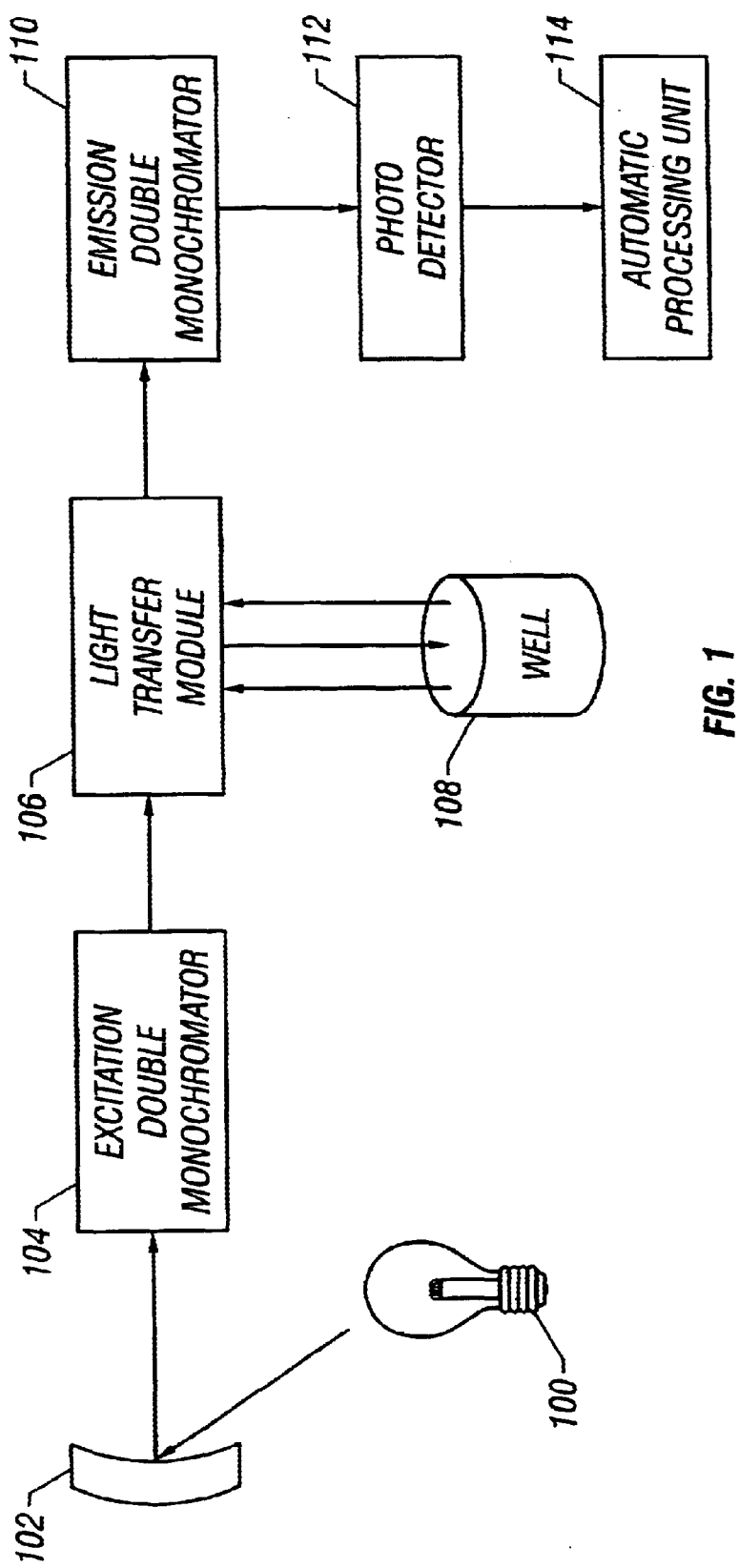
FIG. 1 is a schematic diagram of an embodiment of a fluorescence spectrophotometer system.

FIG. 1 is a schematic diagram of an embodiment of a fluorescence spectrophotometer system in accordance with the present invention. A broadband light source 100 illuminates a mirror 102, which is suitably curved to focus the light onto a double monochromator 104. In alternative configurations, a narrow band light source such as a photodiode or a laser can be substituted for the broadband light source but used with the same monochromator configuration.

Light of the desired wavelength is passed by the double monochromator 104 to a light transfer module (LTM) 106. The LTM 106 directs the excitation light from monochromator 104 onto sample 108, which can be, for example, one well of a microwell plate or one lane of a 1-D polyacrylamide gel. Any resulting fluorescence emitted by the sample is collected by LTM 106 which directs the light to the entrance slit of emission double monochromator 110. The emission monochromator is adjusted to pass wavelengths from the emission spectrum of the fluorophore(s) in the sample and directs those wavelengths to photodetector 112, which measures the energy of the emitted light.

Photodetector 112 may be any suitable photosensitive device, including but not limited to a photomultiplier tube, a phototransistor, or a photodiode. The electronic output of photodetector 112 is applied to an automatic processing unit 114, which generates a signal indicating detection of the selected emission which is stored in a numerical form suitable for further analysis. The automatic processing unit 114 may be, for example, a personal computer having a data collection interface to the spectrophotometer system. In general, all of the elements of the optical pathways in this instrument, including double monochromators 104 and 110 and the LTM 106, should be isolated in light-tight boxes coated internally with non-fluorescent absorptive material to minimize reflectances and light from other sources such a room light.

Figure 2A:
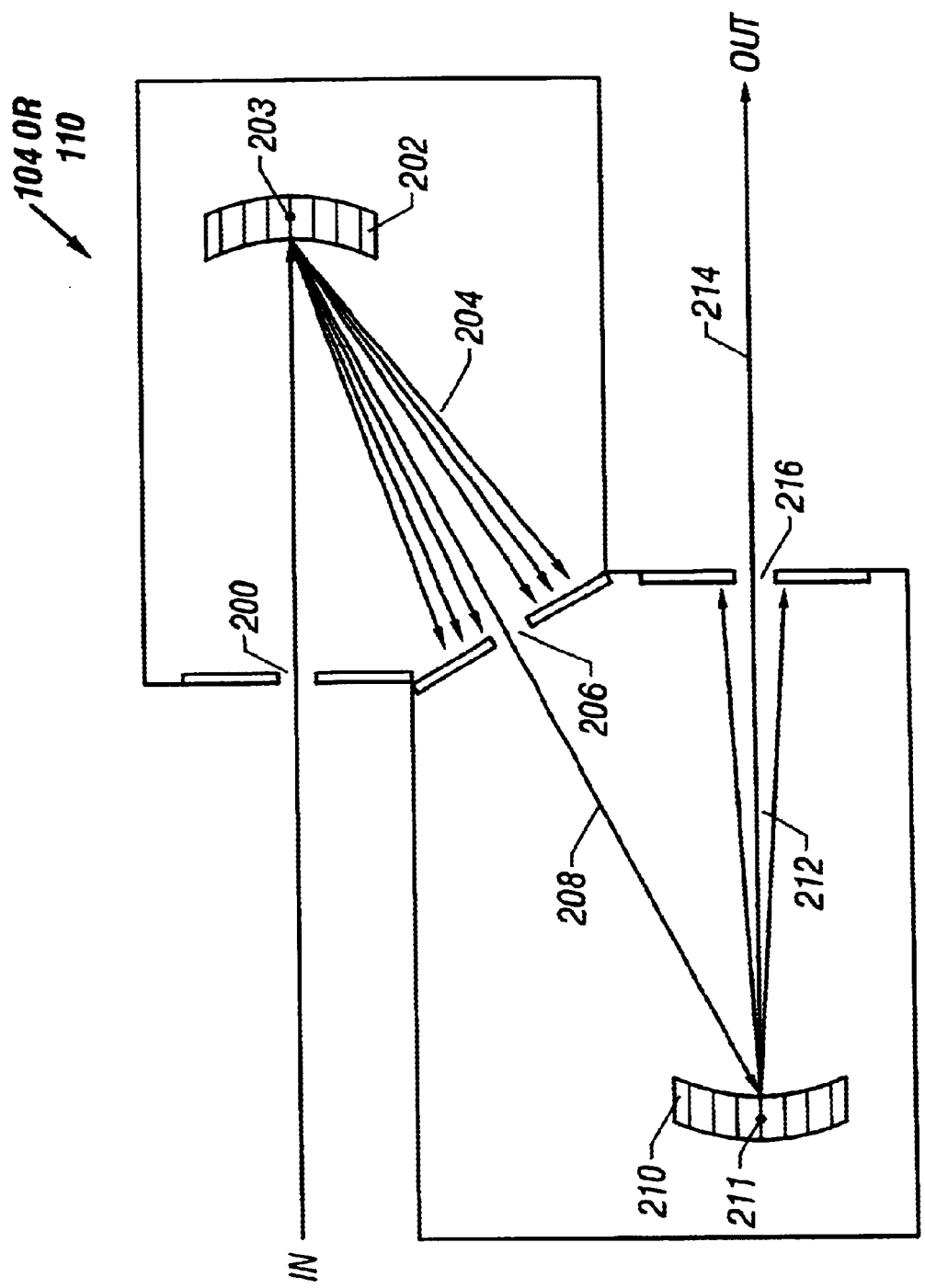
FIG. 2A is a schematic diagram of another embodiment of a double monochromator.

FIG. 2A is a schematic diagram of an embodiment of a double monochromator in accordance with the present invention. The illustrated configuration may be used for either the excitation double monochromator 104 or the emission double monochromator 110.

Broadband light is introduced through a slit 200 in the double monochrormator and reflects off the front surface of a first holographic concave grating 202 that is pivotable around an axis 203. Use of front surface reflection enhances the efficiency of the double monochromator by avoiding absorption of the light within an optical support structure, such as in a rear-surface reflection glass mirror. Use of a concave grating allows the light to be dispersed into selectable wavelengths without the use of supplemental collimating mirrors. This design makes it possible to eliminate two collimating mirrors per grating used in conventional dual monochromator instruments. Use of a holographic grating also reduces astigmatic aberrations and thus decreases the amount of light of unwanted wavelengths ("stray light").

Each double monochromator has three slits: an entrance slit, through which light first enters the monochromator; an internal selection slit; and, an exit selection slit, through which light leaves the monochromator. The first concave grating 202 reflects the wavelengths of the incoming light as a first spatially dispersed beam 204. Each wavelength of this first spatially dispersed beam 204 is reflected at a unique angle relative to other wavelengths. By pivoting the first concave grating 202 around its axis 203, a desired band of wavelengths can be directed through the internal selection slit 206 within the monochromator housing.

The selected range of wavelengths 208 is then reflected off a second holographic concave grating 210 that is pivotable about an axis 211. The second concave grating 210 reflects the wavelengths of the first spatially dispersed beam 204 as a second spatially dispersed beam 212. By pivoting the second concave grating 210 around its axis 211, a desired narrow band of wavelengths 214 can be directed through an exit selection slit 216.

The widths of selection slits 206 and 216 determine the selected wavelengths of light leaving the monochromator. Wider slits allow more light energy to pass through a monochromator, but the light includes a broad range of wavelengths; narrower slits reduce the amount of light passing through a monochromator but narrow the selected range of wavelengths. The use of wider slits increases the sensitivity of detection, which is beneficial in measurements of total fluorescence in an area or volume as would be the case in measurements made in microwells. By contrast, the use of narrow slits increases the spatial resolution which is beneficial in discriminating between different fluorophores at particular locations as is the case with bands separated in a polyacrylamide gel. That is, the smaller the slit dimensions, the smaller the area of detection at the sample. In the case of laser light sources and pinhole slits, the area of excitation at any given moment is a point that corresponds to a particular data pair representing fluorescent intensity and position.

It is a general rule in optical systems that each optical component reduces the efficiency of light throughput.

Advantages of the configuration shown in FIG. 2A include, but are not limited to, elimination of collimating mirrors for redirecting light within the double monochromator, such as is the case with traditional monochromators. In the present embodiment, only two light directing elements (the first and second holographic concave gratings 202, 210) are required, thus improving overall light efficiency.

Figure 2B:
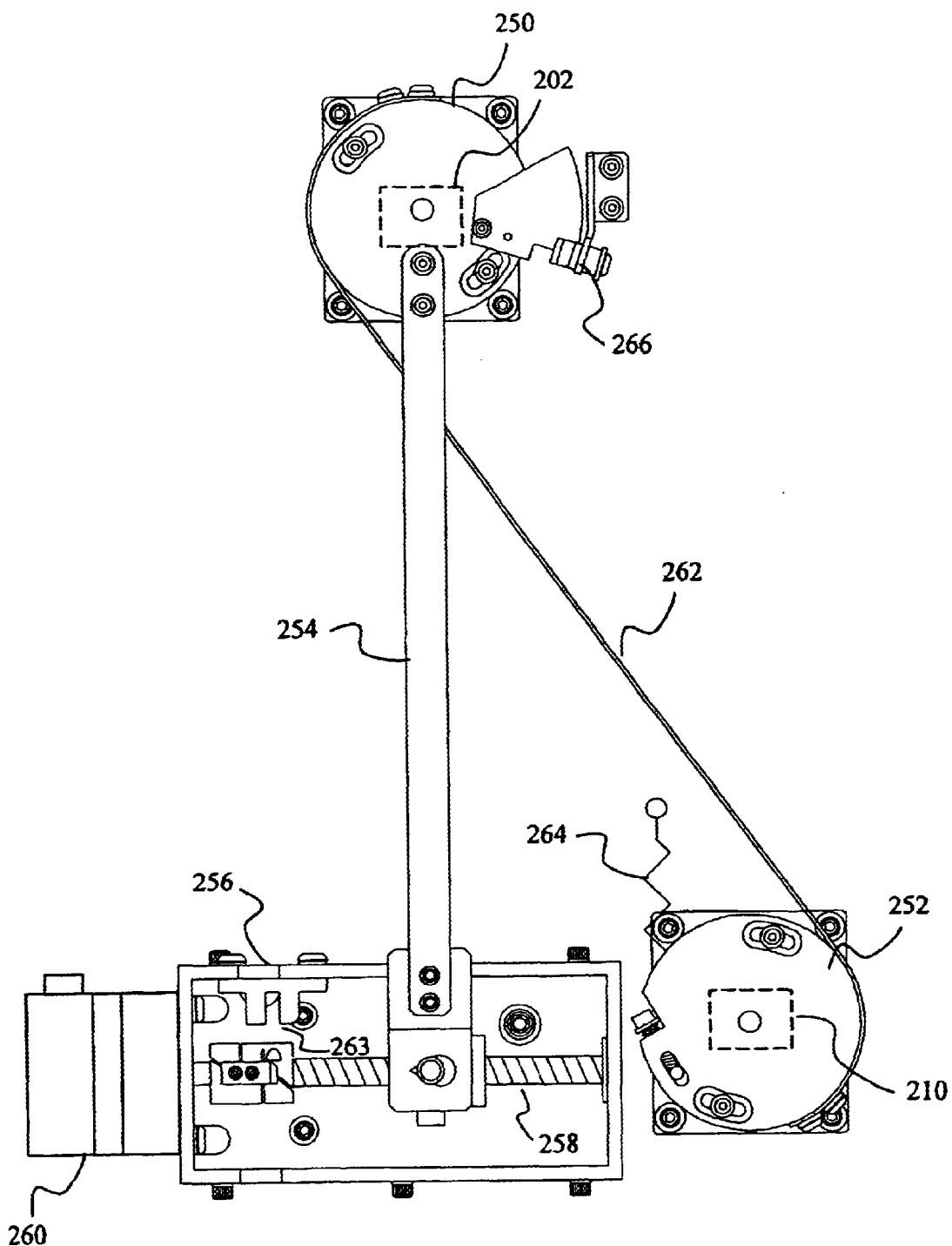
FIG. 2B is a schematic diagram showing a tension band actuator mechanism for pivoting the gratings of the double monochromator shown in FIG. 2A.

In the configuration illustrated in FIG. 2A, the first concave grating 202 and the second concave grating 210 are pivoted oppositely and in tandem by a suitable mechanism. A mechanism according to one embodiment uses a tension band actuator mechanism for pivoting the gratings 202, 210, as shown in FIG. 2B. The gratings 202, 210 are mounted coaxially with pivot wheels 250, 252, respectively. A lever arm 254 is connected to pivot wheel 250 at one end and a screw drive mechanism 256 at the other end. Lever arm 254 is moved along threaded rod 258 as the rod is rotated by motor 260.

Lever arm 254 rotates pivot wheel 250 as it travels along rod 258. Pivot wheel 250 is connected to pivot wheel 252 by a tension band 262. According to the present embodiment, tension band 262 is a 0.003 inch stainless steel band. Tension band 262 causes the pivot wheel 252 and grating 210 to counter-rotate in tandem with pivot wheel 250 and grating 202. A spring 264 connected between a housing and pivot wheel 252 maintains tension in tension band 262. The position of the grating can be determined and controlled by a microcontroller connected to pivot wheel sensor 266 and screw drive sensor 268.

Figure 3:
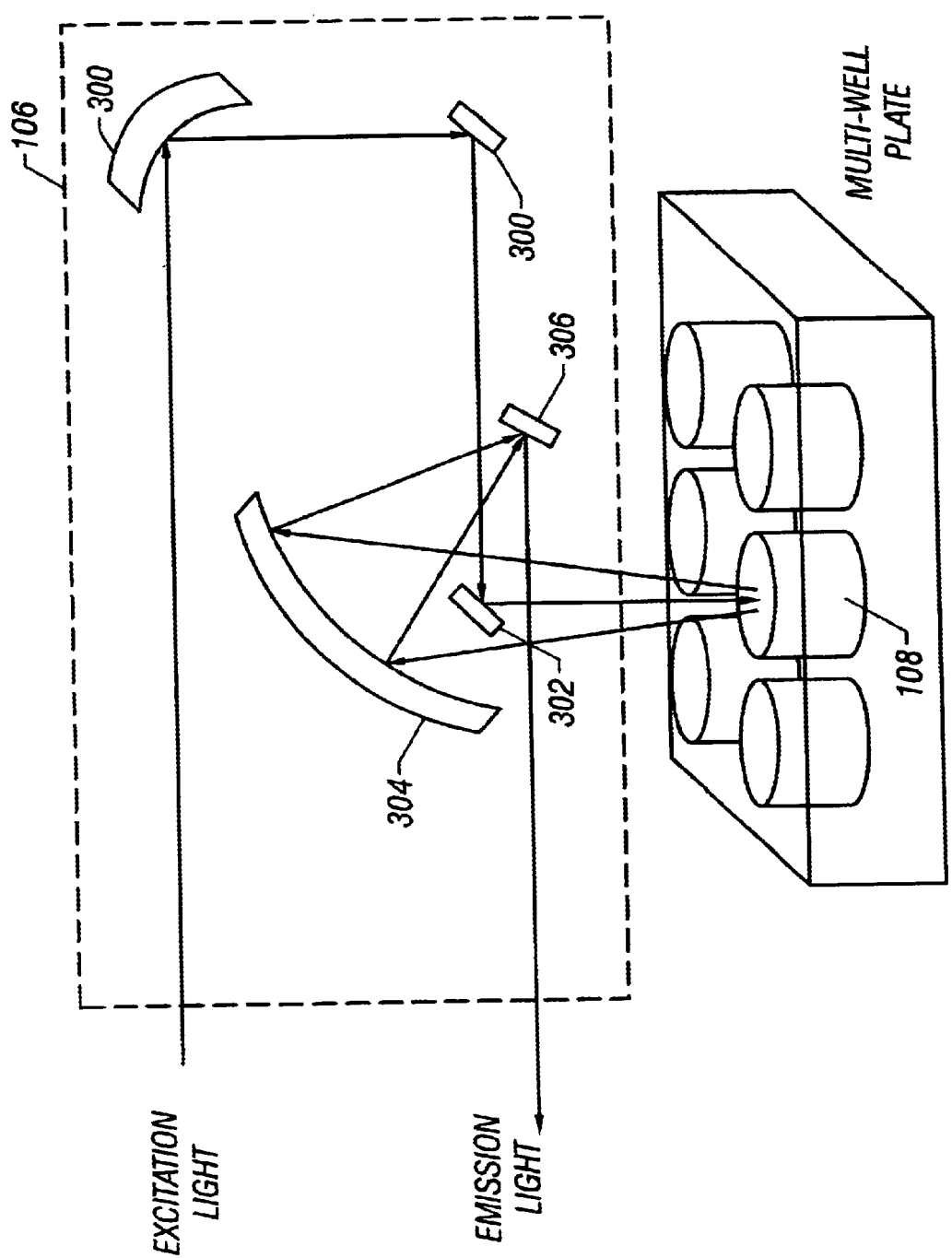
FIG. 3 is a schematic diagram of one embodiment of the light transfer module shown in FIG. 1.

FIG. 3 is a schematic diagram of one embodiment of the LTM 106 shown in FIG. 1. Excitation light enters the LTM 106 through an entrance aperture whereupon it is directed, either with or without one or more mirrors 300, to a coaxial excitation mirror 302. The coaxial excitation mirror 302 may be flat, or have some curvature to focus or disperse light as desired. The coaxial excitation mirror 302 is positioned to direct the excitation light onto the sample 108. More particularly, the coaxial excitation mirror 302 may be positioned somewhat off-axis with respect to sample 108, but should be positioned so that substantially all of the excitation light strikes the sample to achieve maximum illumination.

In one application, each well of a multi-well plate can be positioned beneath the coaxial excitation mirror 302 by X-Y translation of either the LTM 106 or of the multi-well plate. In another application involving monochromators equipped with optional microscope optics, different regions of intact biological cells that have been mounted on glass slides or culture plates can be separately imaged by using optical elements in the light path and by positioning the sample beneath the coaxial excitation mirror 302 by X-Y-Z translation of either the LTM 106 or of the glass slides or culture plates. Any fluorescence emission from one or more fluorophores in a sample is collected by a coaxial emission mirror 304. The coaxial emission mirror 304 must be concave so as to focus and direct the emission light, either directly or by one or more light directing mirrors 306, out of an exit port of the LTM 106. In the embodiment shown in FIG. 3, the emission light exits the LTM 106 from the same side that the excitation light enters the LTM 106. However, different placements of the entrance and exit ports can be used by suitable placement of light directing 300, 306.

The coaxial placement of the excitation mirror 302 and the emission mirror 304 ensures that a high percentage of the excitation light is directed onto the sample within a well 108, and that a high percentage of the fluorescence light emitted from the well opening is collected for analysis.

In the preferred embodiment, all of the mirrors within the LTM 106 comprise front, or "first" surface mirrors. Such mirrors have a reflective material, such as aluminum, coated onto the surface of a substrate, such as glass or ceramic onto which light is directed. The coating serves as the reflective surface, so that light does not penetrate the substrate, as in an ordinary second surface mirror. Such first surface mirrors are substantially more efficient.

It will be understood by one of ordinary skill in the art that a number of different reflecting mirrors may be used to direct the light within the LTM 106, as needed. However, it is desirable that the number of such reflecting surfaces be minimized in order to improve efficiency of the LTM 106. In the preferred embodiment, the coaxial excitation mirror 302 is an elliptical mirror approximately 6×9 millimeters in dimension, while the coaxial emission mirror 304 is approximately 75 millimeters in diameter. Other dimensions can be used and generally will vary with the dimensions of the overall instrument.

Figure 4:
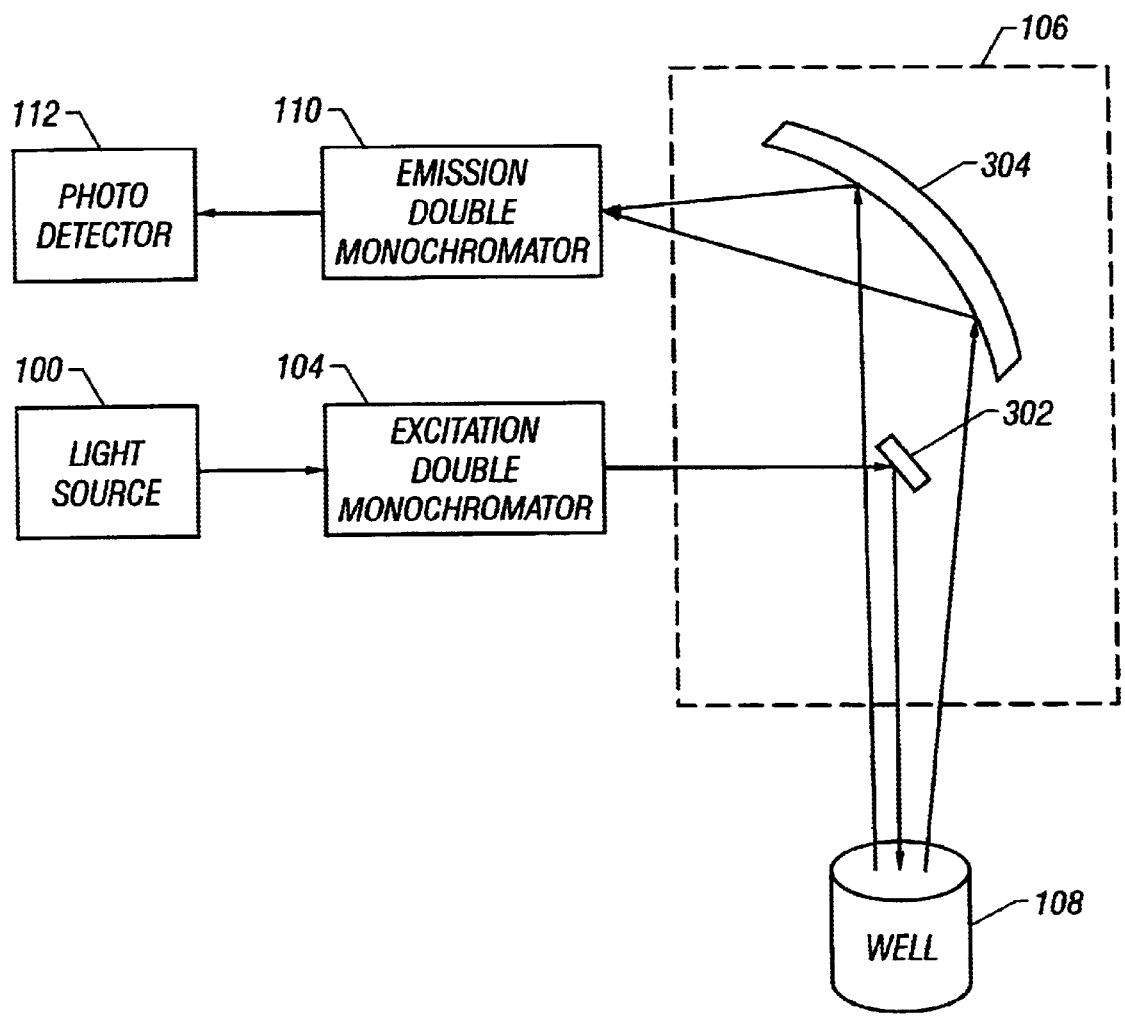
FIG. 4 is a schematic diagram of a simplified version of a fluorescence spectrophotometer in accordance with the present invention.

FIG. 4 is a schematic diagram of a simplified version of a fluorescence spectrophotometer in accordance with an embodiment of the present invention. In this embodiment, excitation wavelengths are selected from a broadband light source 100 by means of an excitation double monochromator 104. The excitation light is directed by a coaxial excitation mirror 302 to a sample within a well 108. Fluorescence emissions are collected and focused by a coaxial emissions mirror 304 that is in reflective alignment with the coaxial excitation mirror 302. The coaxial emissions mirror 304 directs the collected and focused light into an emission double monochromator 110. The emission double monochromator 110 selects a desired emission wavelength and directs that wavelength to a photodetector 112 for counting and analysis. This embodiment minimizes the number of reflective surfaces within the LTM 106.

One aspect of the embodiment shown in FIG. 4 is that its compact configuration allows for use of the instrument as a dual path spectrophotometer. That is, a sample can be excited from both the open side of a well 108 or from the bottom side of the well.

Figure 5A:
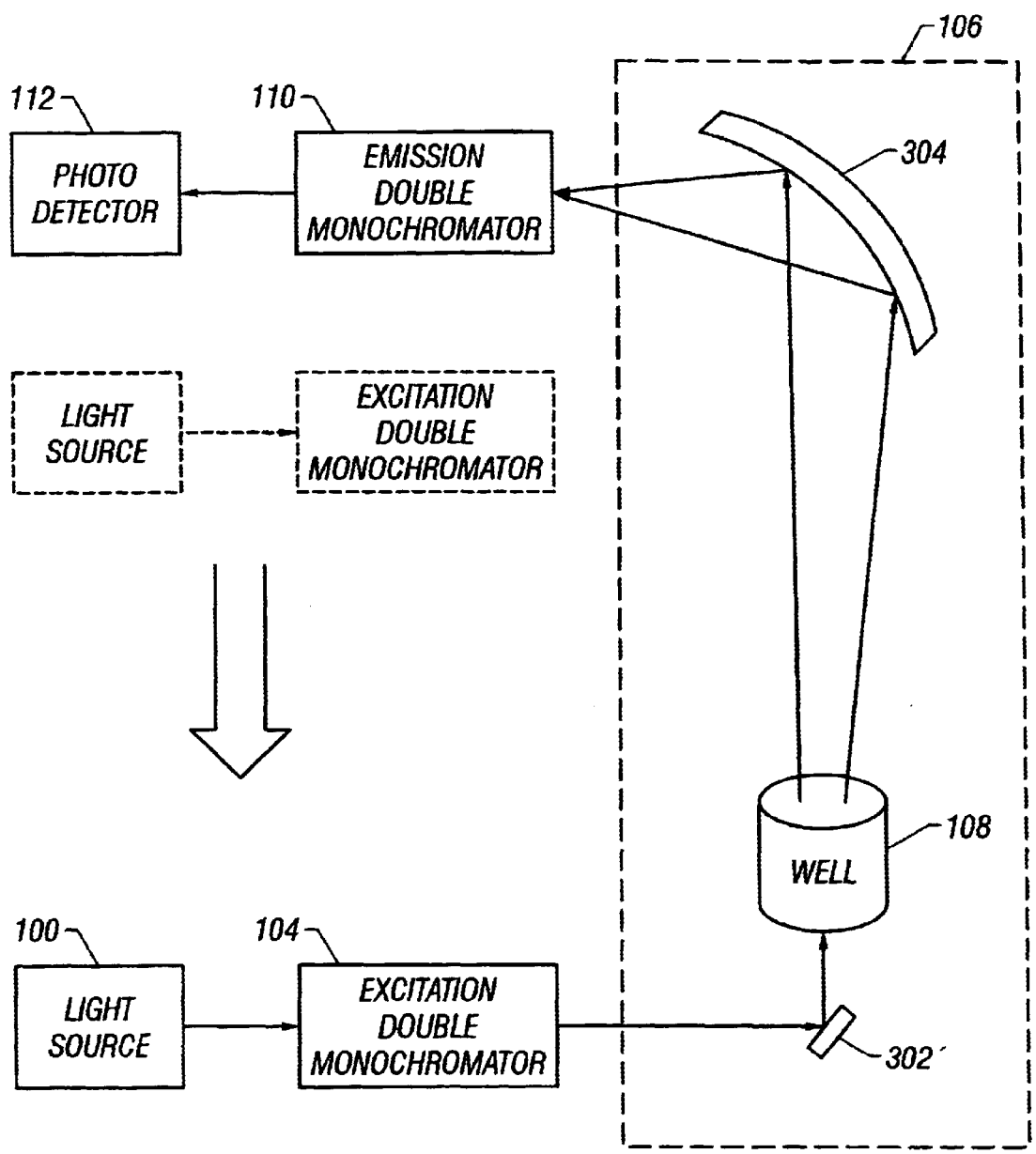
FIG. 5A shows a first alternative dual path embodiment of the invention.

FIG. 5A shows a first alternative dual path embodiment of the invention. One or both of the light source 100 and the excitation double monochromator 104 optionally can be translated from their normal position to a position below a multi-well plate such that excitation light impinges upon a bottom-illumination coaxial excitation mirror 302', which directs excitation light through the transparent bottom substrate of a well 108. (If the light source is not translated, light directing mirrors may be interposed to direct light through the excitation double monochromator 104). Fluorescence emissions emanating from the opening of the well 108 are collected by a coaxial emission mirror 304. When configured for bottom illumination, the top illumination coaxial excitation mirror 302 can be removed from the light path in order to maximize the amount of fluorescent light collected by the emission mirror 304. Alternatively, the top-illumination excitation mirror 302 (not shown in FIG. 5A) can be left in place, as shown in FIG. 4. In either case, the bottom-illumination excitation mirror 302' is in direct alignment (as opposed to reflective alignment) with the emissions mirror 304.

Figure 5B:
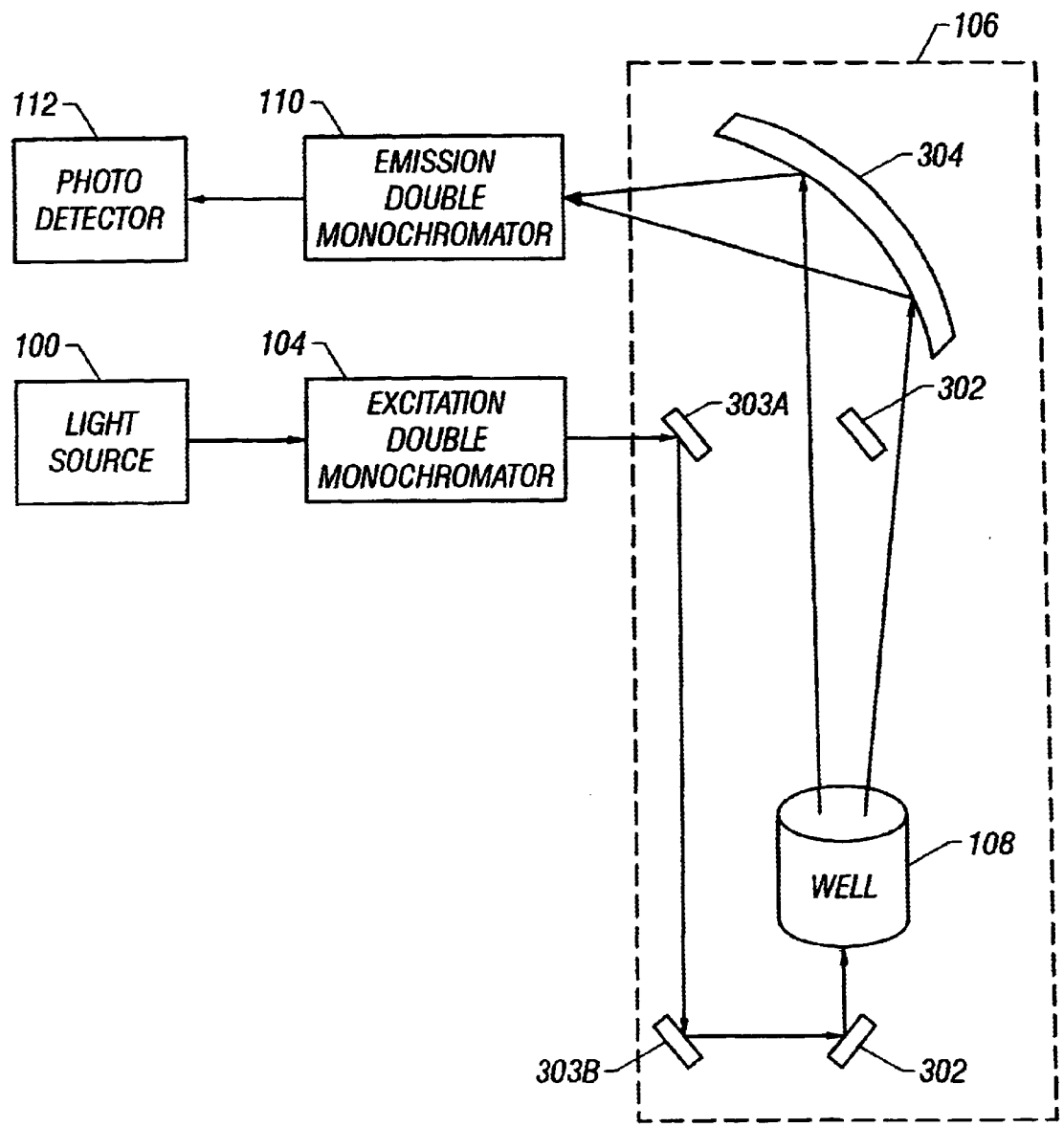
FIG. 5B shows a second alternative dual path embodiment of the invention.

FIG. 5B shows a second alternative dual path embodiment of the invention. In this configuration, for bottom illumination, a set of one or more redirection mirrors 303A, 303B, are interposed into the normal light path from the excitation double monochromator 104 in order to intercept the excitation light. The intercepted excitation light is redirected to impinge upon a bottom-illumination coaxial excitation mirror 302', which directs the excitation light through the transparent bottom substrate of a well 108. The top illumination coaxial excitation mirror 302 may be left in place, as shown, or moved out of position when the redirection mirrors 303A, 303B, are moved into position. Such movement may be accomplished, for example, by translational movement of a carriage on which all four mirrors 302, 303A, 303B, 302', are mounted, into or out of the page. Again, the bottom-illumination excitation mirror 302' is in direct alignment (as opposed to reflective alignment) with the emissions mirror 304.

In all of the configurations shown in FIGS. 4, 5A, and 5B, additional redirection mirrors may be used as desired to suitably guide light to desired locations within the instrument.

According to an embodiment, a timer-counter board that operates at a frequency in excess of 100 MHz is used. The discriminator module can respond to photons at frequencies as high as 30 MHz. The dynamic range of this system ranges from 0 to more than $30 \times 10^6$ photons, thereby eliminating the dynamic range limitations which previously restricted the use of photon counting in fluorescence detection. If the observed current from the PMT is greater than a prescribed threshold established at the discriminator, a 5 volt electrical pulse having a duration of approximately 2 nanoseconds is produced; the timer counter circuit enumerates these pulses as a function of time, that is, establishes a direct quantitation for photons per unit time.

In a spectrophotometer according to one embodiment, a pre-cast polyacrylamide gel containing fluorescently labeled nucleic acids or proteins was placed on a flat plate in the positioning mechanism of the present invention directly under the LTM. With the excitation and emission monochromators set at wavelengths suitable for the fluorescent labels, the gel was moved back and forth under the LTM until all of the gels area had been traversed. At each point of this travel, a fluorescent reading was made and stored as a two dimensional array representing the fluorescent emission at each point of the gel. The distance between the points was adjusted to yield the best response for a given data acquisition time. In the actual experiments, the gel was also scanned as "lanes" representing the path of electrophoresis from the sample well at the top of the gel to the base of the gel because the fluorophores in an electrophoresis gel are arrayed in a line rather than as a point. Each such lane was scanned from the sample well to the bottom of the gel to achieve a substantial reduction in overall data collection time. As a reference for background, a blank lane was scanned and the data subtracted on a point-by-point basis from the corresponding data for lanes containing fluorophores. The corrected data were then analyzed in two ways. In one analysis, an image was constructed of the original gel which was compared to standard laboratory photographs of the same gel for evaluation of standard gel parameters such as migration distance, separation of molecules and concentration of molecular species as determined separately by the digital image and the film. In the other analysis, a "densitometry" plot equivalent to those made for gel lanes from autoradiography films using flat bed scanning detectors was created. From the database relating fluorescence intensity of a lane, the center of each fluorescent band was identified and a cross sectional graph of fluorescent intensities as a function of migration distance was prepared. From the use of gels prepared with different but known amounts of the same fluorescent labeled nucleic acids, a standard curve establishing lower and upper limits of sensitivity, resolution, and overall dynamic range for gel detection were determined.

The "square intensity point spread function" and the "long penetration depth" properties of one and two photon absorption processes have been recognized as important features in future developments in fluorescence detection. Both are accomplished by focusing a femtosecond short pulse laser onto a focal plane in a sample to be studied for fluorescence. In a spectrophotometer according to another embodiment, a laser beam from an appropriate laser was substituted for the quartz halogen or xenon light source used for excitation. The laser beam was used to illuminate the entrance slit of the excitation monochromator. Additional modifications where needed in some cases included, for example, the use of one or two pinhole slits rather than the standard rectangular slits, and the insertion of an objective lens to focus the light after it had passed through the monochromator. The fluorescence emission was collected through the light transfer module as previously and the fluorescence measured as a function of time, or in the cases of image formation and area scanning, as a function of time and position of the light transfer module over the sample as described in gel analysis, above. In this configuration, a pinhole exit slit on the excitation monochromator was used to image light onto a specimen and each point of the image used to excite fluorescence. Moving the sample position in an x-y-z fashion, enabled scanning of areas of the sample to create an image or database. For confocal microscopy, two pinhole slits were required as described below. For multi-photon applications, only a single pinhole slit was used as the exit slit of the excitation monochromator. For two-photon excitation, a microlens array could be used if needed to focus the beam for high transmittance. In general, the configuration was epi-fluorescent although in certain polarization applications, excitation was from the bottom and collection of light from the top.

In yet another embodiment, the present invention was applied in the creation of a scanning fluorescence polarization detector. Fluorescent molecules in solution, when excited with plane-polarized light, will emit light back into a fixed plane (i.e., the light remains polarized) if the molecules remain stationary during the fluorophore's period of excitation (excited state lifetime). Molecules in solution, however, tumble and rotate randomly, and if the rotation occurs during the excited state lifetime and before emission occurs, the planes into which light is emitted can be very different from the plane of the light used for the original excitation.

The polarization value of a molecule is proportional to its rotational relaxation time, which by convention is defined as the time required for a molecule to rotate through an angle of 68.5°. Rotational relaxation time is related to the solution viscosity ($\eta$), absolute temperature (T), molecular volume (V), and the gas constant (R):

Polarization value ∝ Rotational Relaxation Time $$\text{Polarization value} \propto \text{Rotational Relaxation Time} = \frac{3\eta V}{RT}$$

If viscosity and temperature are constant, the polarization is directly related to molecular volume (molecular size), which, in general, correlates well with molecular weight. Changes in molecular volume result from several causes, including degradation, denaturation, conformational changes, or the binding or dissociation of two molecules. Any of these changes can be detected as a function of changes in the polarization value of a solution. Specifically, a small fluorescent molecule which rotates freely in solution during its excited state lifetime can emit light in very different planes from that of the incident light. If that same small fluorophore binds to a larger molecule, the rotational velocity of the small molecule decreases and the effect is detected as a decrease in the polarization value. Measurement of the effect requires excitation by polarized light which can be obtained using a laser or through light selection using a polarizing filter which only transmits light traveling in a single plane. In one experiment, the light of a defined wavelength obtained from the excitation monochromator of the present invention was further refined by passing the light through a polarizing filter designated the "polarizer", to obtain monochromatic, plane-polarized light for excitation (for the present purposes designated "vertically polarized light"). Concurrently, the light path for collecting the emitted light was similarly modified by introduction of a second polarizing filter, designated the "analyzer", which could be rotated to positions either vertical or horizontal to the plane of the exciting light. When a fluorescent sample is solution was introduced into the light path between the "polarizer" and the "analyzer", only those molecules which were oriented properly to the vertically polarized plane absorbed light, became excited, and subsequently emitted light. By rotating the analyzing filter, the amount of emitted light in the vertical and horizontal planes could be measured and used to assess the extent of rotation of the small fluorescent molecule in the solution before and after binding to a larger molecule.

In yet another application, the invention was utilized in confocal microscopy, a method for eliminating one of the fundamental difficulties of fluorescence microscopy, namely the reduction in spatial resolution at the focal plane of the microscope owing to out-of-focus light. A spectrophotometer according to another embodiment was used to create a novel confocal microscope from the embodiment essentially as described under laser excitation above to focus a light image on whole cell mounts and achieve both multiple and single photon excitation of the fluorescent labels in a sample. Fluorophores in planes out of the focus were not illuminated and did not fluoresce.

In confocal imaging, apertures were used in both the excitation and emission light paths in order to focus a cone of light through the specimen and in the emission light path in order to eliminate scattered and out-of-plane fluorescence. The development of mode locked dye lasers has made simultaneous multiphoton excitation practical because such lasers are capable of delivering the available excitation energy to a focal spot in very brief pulses and with sufficient energy to achieve two photon excitation. In multiphoton imaging, the focal spot provided by the laser excites a sufficiently small volume that, when used in conjunction with the light transmission module of this invention, makes it possible to collect all emission light without a second pinhole slit on the emission side. No emission aperture changes were necessary.

A number of embodiments of the present invention have been described. Nevertheless, it will be understood that various modifications may be made without departing from the spirit and scope of the invention. For example, the double monochromators of the invention can be used in other types of instruments, and the LTM may be used in a filter-based spectrophotometer or other optical instruments. As a further example, the LTM may be used to direct input light to an area to be illuminated and efficiently collect, focus, and direct light emitted (e.g., either by reflection or by fluorescence) from the illuminated area. Accordingly, other embodiments are within the scope of the following claims.

What is claimed is:

1. A fluorescence spectrophotometer system including:
    (a) a light source;
    (b) a first double monochromator operating to separate and output selected wavelengths of light from the light source as excitation light;
    (c) a reflection light transfer module for directing substantially all of the excitation light directly onto a sample, and for collecting, focusing, and directing fluorescence light emitted from the sample as emission light;
    (d) a second double monochromator operating to separate and output selected wavelengths of the emission light; and
    (e) a photodetector and analyzer for detecting the selected wavelengths of emission light and outputting an indication of such detection.

2. The fluorescence spectrophotometer system of claim 1, wherein the first double monochromator or the second double monochromator includes:
    (a) an entrance slit for accepting light;
    (b) a first optical grating positioned to intercept and disperse the accepted light from the entrance slit;
    (c) a first selection slit positioned to intercept at least part of the dispersed light from the first optical grating and select and pass a narrowed range of wavelengths from such dispersed light;
    (d) a second optical grating positioned to intercept and disperse the passed light from the first selection slit; and
    (e) a second selection slit positioned to intercept at least part of the dispersed light from the second optical grating and select and pass a narrowed range of wavelengths from such dispersed light.

3. The fluorescence spectrophotometer system of claim 2, wherein the first optical grating and the second optical grating are both concave gratings.

4. The fluorescence spectrophotometer system of claim 3, wherein the concave gratings are holographic concave gratings.

5. The fluorescence spectrophotometer system of claim 2, wherein the first optical grating and the second optical grating pivot about axes of rotation for selecting a desired range of wavelengths of light as a function of angle of rotation.

6. The fluorescence spectrophotometer system of claim 2, further including a band drive, coupled to each of the first optical grating and the second optical grating, for rotating the first optical grating and the second optical grating synchronously.

7. The fluorescence spectrophotometer system of claim 1, wherein the reflection light transfer module includes:
    (a) an excitation mirror, positioned substantially coaxial with a well containing the sample, for directing excitation light to illuminate the sample; and
    (b) an emission mirror, positioned substantially coaxial with the well containing the sample, for collecting, focusing, and directing fluorescence light emitted by the sample.

8. The fluorescence spectrophotometer system of claim 7, wherein the emission mirror is a spherical mirror.

9. The fluorescence spectrophotometer system of claim 7, wherein the excitation and emission mirrors are first-surface mirrors.

10. The fluorescence spectrophotometer system of claim 7, wherein the excitation mirror is positioned to direct excitation light into an opening of the well, and the emission mirror is positioned to collect fluorescence light emitted from the opening of the well.

11. The fluorescence spectrophotometer system of claim 7, wherein the well has a transparent bottom substrate, and the excitation mirror is positioned to direct excitation light into the well through the transparent bottom substrate, and the emission mirror is positioned to collect fluorescence light emitted from a top opening of the well.

12. The fluorescence spectrophotometer system of claim 11, wherein one or both of the light source and first double monochromator are moved to direct excitation light directly onto the excitation mirror.

13. The fluorescence spectrophotometer system of claim 11, wherein one or more light directing mirrors are positioned to direct excitation light from the first double monochromator to the excitation mirror.

14. The fluorescence spectrophotometer system of claim 1, wherein the photodetector and analyzer counts the number of photons of the detected selected wavelengths of emission light.

* * * * *